(12) United States Patent
Koerner et al.

(10) Patent No.: US 7,779,830 B2
(45) Date of Patent: *Aug. 24, 2010

(54) DOSING DEVICE

(75) Inventors: Joachim Koerner, Uhldingen (DE);
Michael Helmlinger, Radolfzell (DE);
Holger Schuerle, Radolfzell (DE)

(73) Assignee: Ing. Erich Pfeiffer GmbH, Radolfzell (DE)

( * ) Notice: Subject to any disclaimer, the term of this patent is extended or adjusted under 35 U.S.C. 154(b) by 878 days.

This patent is subject to a terminal disclaimer.

(21) Appl. No.: 11/051,961

(22) Filed: Feb. 4, 2005

(65) Prior Publication Data

US 2005/0252508 A1 Nov. 17, 2005

(30) Foreign Application Priority Data

Feb. 5, 2004 (DE) .................. 10 2004 006 450

(51) Int. Cl.
*B65D 83/06* (2006.01)
*F16K 31/02* (2006.01)
*A61G 10/00* (2006.01)
*A61M 11/00* (2006.01)
*A61M 16/00* (2006.01)

(52) U.S. Cl. .................. 128/200.16; 128/200.14; 128/200.23; 128/204.23; 128/200.11; 128/200.12; 128/200.18; 128/203.15; 128/205.26

(58) Field of Classification Search ............ 128/200.14, 128/200.16, 200.21, 200.23, 203.12, 203.13, 128/203.14, 203.15, 203.19, 203.21, 203.23, 128/204.23, 200.11, 200.12, 200.18, 205.26
See application file for complete search history.

(56) References Cited

U.S. PATENT DOCUMENTS

| 4,294,407 | A | | 10/1981 | Reichl et al. | |
|---|---|---|---|---|---|
| 5,134,993 | A | * | 8/1992 | van der Linden et al. | 128/200.14 |
| 5,452,711 | A | | 9/1995 | Gault | |
| 5,569,190 | A | | 10/1996 | D'Antonio | |
| 5,743,252 | A | * | 4/1998 | Rubsamen et al. | 128/200.14 |
| 5,755,218 | A | * | 5/1998 | Johansson et al. | 128/200.14 |
| 5,893,515 | A | | 4/1999 | Hahn et al. | |
| 6,435,175 | B1 | * | 8/2002 | Stenzler | 128/200.14 |

(Continued)

FOREIGN PATENT DOCUMENTS

DE 28 31 970 A1 2/1980

(Continued)

OTHER PUBLICATIONS

German Patent Office Search Report dated Nov. 22, 2004 (3 pages).

(Continued)

*Primary Examiner*—Patricia M Bianco
*Assistant Examiner*—Nihir Patel
(74) *Attorney, Agent, or Firm*—Flynn, Thiel, Boutell & Tanis, P.C.

(57) ABSTRACT

A dosing device with an electromechanical interface is provided. The dosing device includes delivery means, a medium reservoir and an applicator, on the one hand, and a control unit and electrical energy store, on the other hand, in separate structural units. Guide means are provided for fitting one of the structural units into the other structural unit. The guide means has an electromechanical interface for coupling and/or uncoupling relative to the control unit and/or energy store without using tools.

4 Claims, 2 Drawing Sheets

U.S. PATENT DOCUMENTS

| | | |
|---|---|---|
| 6,981,499 B2 * | 1/2006 | Anderson et al. ...... 128/200.23 |
| 7,234,459 B2 * | 6/2007 | Del Bon ................. 128/200.21 |
| 2004/0192044 A1 | 9/2004 | Degertekin et al. |
| 2004/0195394 A1 | 10/2004 | Cornet et al. |
| 2005/0054208 A1 | 3/2005 | Fedorov et al. |
| 2005/0139465 A1 | 6/2005 | Kasuya et al. |
| 2006/0032941 A1 | 2/2006 | Sheng-Chih et al. |

FOREIGN PATENT DOCUMENTS

| | | |
|---|---|---|
| DE | 2854841 B1 | 6/1980 |
| DE | 92 04 844.7 U1 | 9/1992 |
| EP | 0 373 237 A1 | 6/1990 |
| EP | 0 897 755 A2 | 2/1999 |
| EP | 1 533 041 A1 | 5/2005 |
| WO | WO 2005/025654 A1 | 3/2005 |
| WO | WO 2005/107946 A2 | 11/2005 |
| WO | WO 2006/112357 A1 | 10/2006 |

OTHER PUBLICATIONS

European Patent Office Search Report dated Feb. 13, 2008 (3 pages).
European Patent Office Search Report dated Sep. 16, 2008 (5 pages).
European Patent Office Search Report dated Nov. 13, 2008 (17 pages).

* cited by examiner

DOSING DEVICE

FIELD OF THE INVENTION

The invention relates to a dosing device with a delivery means for at least one medium, with a medium reservoir for storing the medium and with an applicator for dispensing the medium, and with a control unit for acting on the delivery means and an electrical energy store for powering the control unit and/or the delivery means.

BACKGROUND OF THE INVENTION

Many designs of dosing devices of this kind are known from the prior art. They are used for administering powdery or liquid active substances in areas such as cosmetics or pharmacy. In one known type of dosing device, as is described in DE 2854841 C2, a medium reservoir is provided in which the medium to be dispensed is stored until the time of a dispensing operation. During the dispensing operation, the medium is conveyed from the medium reservoir by an electrically driven delivery means and can be dispensed through an applicator into an environment of the dosing device. To ensure precise dosing of the dispensed medium, a control unit is provided which acts on the delivery means and can control the dispensing of the medium. To operate the control unit and the delivery means, an electrical energy store is provided on the dosing device.

The object of the invention is to make available a dosing device of the type mentioned at the outset which can be produced particularly economically and can be operated particularly economically.

This object is achieved by the fact that the delivery means, medium reservoir and applicator, on the one hand, and the control unit and electrical energy store, on the other, are accommodated respectively in separate structural units, and by the fact that guide means are provided for fitting the structural units one into the other, said guide means having an electromechanical interface for coupling and/or uncoupling relative to the control unit and/or energy store without using tools. By integrating all the medium-conveying components, such as delivery means, medium reservoir and applicator in one common structural unit, it is possible to do without complicated coupling and/or sealing measures between the medium-conveying components such as delivery means, medium reservoir and applicator. By integrating the control unit and the energy store in a second structural unit, the number of electrical contacts and the line length of electrical connections can be kept to a minimum. In this way, a simpler, more reliable and less expensive design of the dosing device is possible. The guide means can be of a linear or non-linear configuration. The guide means preferably have rectilinear guides or curved guides with or without inclination. On account of the guide means and the electromechanical interface, a connection can be particularly easily established between the structural units. The guide means provide a user with assistance when assembling and mechanically locking the structural units. By contrast, the electromechanical interface affords the necessary electrical contacts between the structural units. The user therefore only has to couple the structural units together to immediately obtain, without any further measures, an operational dosing device.

In one embodiment of the invention, the guide means have mutually corresponding linear guide profiles on both structural units. When coupling the structural units together, these linear guide profiles limit a movement clearance between the structural units to a linear assembly movement and thus ensure correct connection of the structural units via the electromechanical interface. The linear assembly movement permits particularly simple and user-friendly coupling and uncoupling of the structural units.

In a further embodiment of the invention, one structural unit is provided with a receiving chamber which is open towards one end and into which a corresponding plug-in portion of the other structural unit can be introduced. In this way, the guide means, locking means and sensitive parts of the electromechanical interface can be accommodated in a protected position in the receiving chamber. The corresponding plug-in portion can be limited to simple and robust geometries and is thus safer when handled by the user.

In a further embodiment of the invention, electrical contact surfaces of the electromechanical interface are provided in the area of the receiving chamber and of the plug-in portion. When operatively connected to corresponding contact tongues, the contact surfaces permit transmission of electrical signals between the structural units after the plug-in portion has been fitted into the receiving chamber, without special measures having to be taken by the user to do this.

In a further embodiment of the invention, the receiving chamber and the plug-in portion at least in some sections delimit an air channel for a defined delivery of air to the applicator. The air channel serves to provide a defined stream of air which is taken from the environment and, depending on the requirements of the medium-dispensing operation, is conveyed as a laminar or turbulent flow through the dosing device and into the applicator. The stream of air is in this case generated in particular by an inhalation movement on the part of the user between whose lips an applicator designed as a mouthpiece is firmly held. The underpressure produced during the inhalation movement causes air to flow along the air guidance means through the mouthpiece, in particular into the pharynx, bronchi or lungs of the user. With the defined stream of air, it is possible to achieve a particularly advantageous dosing of the medium to be dispensed.

In a further embodiment of the invention, the applicator is mounted on the structural unit so as to be movable between a rest position and a dispensing position. In the rest position, a closure means can protect the applicator against contamination by microbes or particles of dirt. By moving the applicator into the dispensing position, an applicator opening is freed and medium can be dispensed. The movable arrangement means that the user can select a comfortable and advantageous orientation of the applicator and thus safely dispense the medium.

In a further embodiment of the invention, the control unit has sensor means for detecting an end position of the applicator, and the delivery means can be set by the control unit in such a way that, in the dispensing position of the applicator, a stream of medium is released and, in the rest position of the applicator, the stream of medium is held back. The sensor means, which transmit a sensor signal concerning a position of the applicator to the control unit, it is possible to prevent medium from being dispensed when the applicator is in the rest position. Particularly if a closure means is present, it is thus possible to avoid incorrect dosing which could lead to undesired consequences such as damage to the dosing device or accumulation of active substances, contained in the medium, in the applicator.

In a further embodiment of the invention, catch means are provided between the two structural units and, depending on the position of the movable applicator, can be moved into a release position or into a locking position. The catch means prevent undesired unlocking of the structural units and thus contribute to correct functioning of the dosing device. To unlock the structural units, the user has to move the applicator from the locked position, which can also cover quite a large locking range, to a release position. In one advantageous embodiment of the dosing device, the applicator is provided with pretensioning means which necessitate application of force by the user in order to unlock the structural units.

In a further advantageous embodiment of the invention, the catch means have mechanical forced guidance means which, in the end positions of the applicator, lock the two structural units together and, in at least one intermediate position of the applicator, release the structural units for separating them from one another. In this way it is possible to obtain a structurally simple design of the catch means, and in which simple operation is also ensured. The forced guidance means permit separation of the structural units preferably only in an exactly defined intermediate position of the applicator, whereas in all other positions of the applicator, including the end positions, no separation of the structural units is possible.

In a further embodiment of the invention, a dispensing area of the applicator is provided with, in particular, antimicrobial active substances for reducing the number of microorganisms. The active substances are provided to avoid contamination and fouling of medium-conveying surfaces in the applicator and they serve to reduce associated risks for the person using the dosing device. The active substances are in particular antimicrobial and can be provided on or in the medium-conveying surfaces of the applicator, especially by application or incorporation of copper-containing or silver-containing substances. Alternatively, the active substances can also be formed by a sponge arrangement which takes up residual droplets at the outlet opening of the applicator and can thus prevent or at least reduce contamination.

Further advantages and features will become evident from the claims and from the following description of a preferred illustrative embodiment of the invention in which reference is made to the drawing.

DETAILED DESCRIPTION

Figure 1:
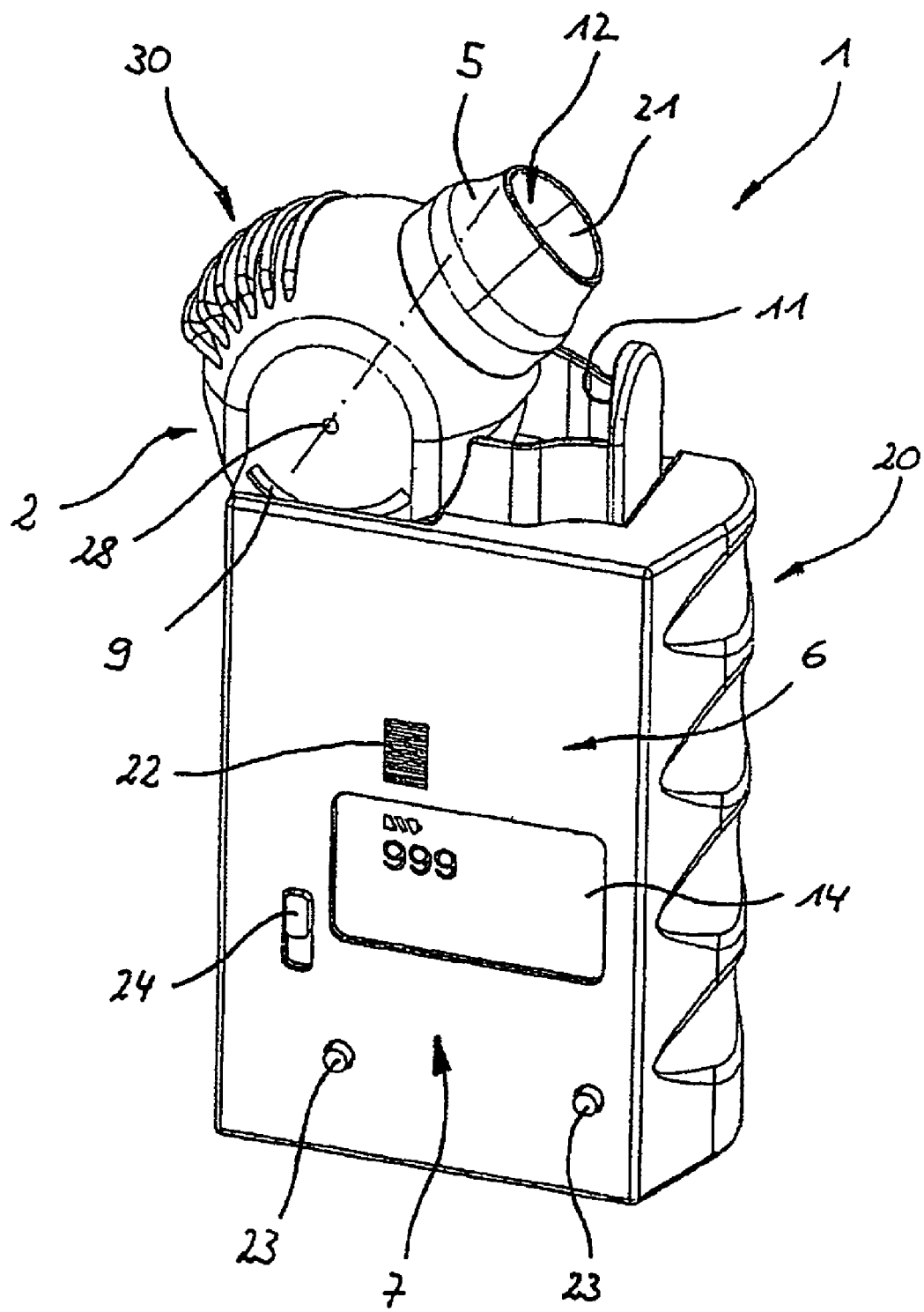
FIG. 1 shows, in isometric representation, a dosing device made up of two structural units.

A dosing device 1 according to FIG. 1 has a first structural unit which is designed as an ultrasonic atomizer 2 and which is fitted into a second structural unit with a base housing 20.

Figure 2:
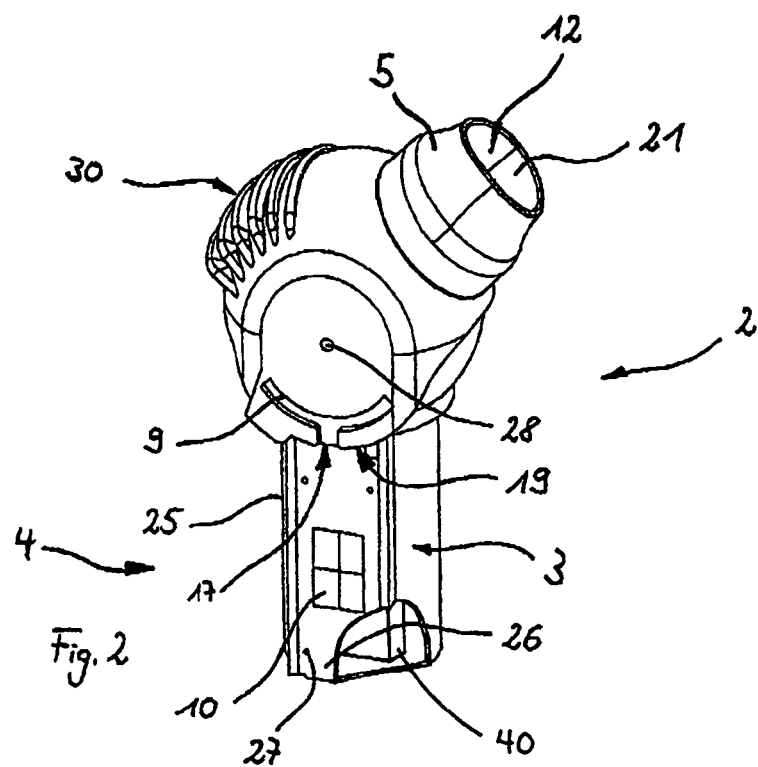
FIG. 2 shows, in isometric representation, an ultrasonic atomizer.

The ultrasonic atomizer 2 shown in FIG. 2 is provided with a plug-in portion 4 of substantially constant cross section. Linear guide tracks 25 are formed on the cross section and are provided for operative connection to corresponding guide tracks 25 of the base housing 20. The plug-in portion 4 comprises an electrically driven delivery means 40 (shown schematically) and also a medium reservoir 3 (not shown in detail) and is connected to an applicator designed as mouthpiece 5. The electrically driven delivery means can be designed in particular as an electromechanical or electronic medium pump, followed downstream by an ultrasonic atomization of the delivered medium. The medium reservoir 3 can in particular be designed as an unpressurized container, as a temporarily pressurized container, or as a pressurized container with permanent internal pressure, and it is filled with the medium that is to be dispensed. Suitable materials for the medium reservoir 3 are in particular glass, plastic or metal. For the at least temporary generation of a pressure in the medium, mechanical or pneumatic pressure-generating means in particular can be provided in the medium reservoir 3. Suitable mechanical pressure-generating means are, in particular, medium reservoir sections that are deformable by external forces, or movable pistons acted on by mechanical or electromechnical actuating means.

The mouthpiece 5 is arranged on the ultrasonic atomizer 2 so as to be able to swivel about a pivot hinge 28 and is acted upon with a restoring force by pretensioning means (not shown). The mouthpiece 5 has a mouthpiece opening 12 through which a mixture of medium to be dispensed and air can be sucked by a user. On an inwardly directed medium-conveying surface designed as mouthpiece wall 21, the mouthpiece 5 has an antimicrobial coating which, when the dosing device 1 is not used for some time, prevents an accumulation of microorganisms or other contamination. Locking grooves 9 are provided laterally on the mouthpiece 5 and can serve as slides for a locking pin 15 provided in the base housing 20. The locking grooves 9 permit a form fit between the mouthpiece 5 and the base housing 20 while at the same time providing mobility. In the representation in FIG. 1, the dosing device 1 is ready for dispensing of medium, for which purpose the mouthpiece 5 has been deflected from a rest position, by the user applying a force to an operating zone 30, and has been swivelled about a rotation axis directed through a pivot hinge 28 so as to bring it into an operating position.

Provided on a side face of the shaft-shaped plug-in portion 4 of the ultrasonic atomizer 2 there is a flat, flexible printed circuit board 26 which has electrical contact faces 10 and which is connected to the delivery means 40 and/or the ultrasonic atomizer. The printed circuit board 26 is fixed to the surface of the ultrasonic atomizer 2 by locking pins 27.

As can be seen from FIG. 3, guide tracks 25 are provided in a receiving area 8 of the base housing 20 and serve to guide the ultrasonic atomizer 2. Other components of the electromechnical interface, such as spring-tensioned electrical contact tongues 42 for contact with the corresponding electrical contact surfaces 10 of the ultrasonic atomizer 2, are likewise provided in the receiving area 8. The guide tracks 25 permit simple fitting of the plug-in portion 4 into the receiving chamber 8, and clamping means (not shown) with locking lugs for form-fit locking of the plug-in portion 4 are provided. In this way, the electromechanical interface can be used to transmit both mechanical retaining and/or adjusting forces and also electrical and/or electronic signals. The electrical signals are in this case used to act on the dosing device and to transmit measurement values or adjustment values back to the control unit.

A control unit designed as electronic control system 6 (not shown in detail) and an energy store (likewise not shown in detail) designed as accumulator 7 are also provided in the base housing 20. The electronic control system 6 is provided for setting the electrically driven delivery means 40 and can be activated by operating means. These operating means include a slide switch 24 with which the ultrasonic atomizer 2 is locked into and unlocked from its position of insertion in the base housing 20, and several push buttons 23 which are provided for increasing or reducing the dosing quantity in a dispensing operation. Sensor means (not shown in detail) are also provided on the mouthpiece 5 and detect end positions of the mouthpiece 5, and these sensor means can emit electrical signals to the electronic control system 6.

The base housing 20 is provided with an air inlet 22 which extends as a channel through the base housing 20 and, in FIG. 1, is operatively connected to the ultrasonic atomizer 2. A stream of air flowing in through the air inlet 22 is routed between the plug-in area 4 and the receiving area 8 and is conveyed via the electromechanically interface into the mouthpiece 5. The stream of air is in this case produced in particular by an inhalation movement on the part of the user who secures the mouthpiece 5 firmly between his lips and then breathes in. The underpressure produced during the inhalation movement causes air to flow into the air inlet 22 and through the base housing 20 into the mouthpiece 5, and from there in particular into the pharynx, the bronchi or lungs of the user.

Figure 3:
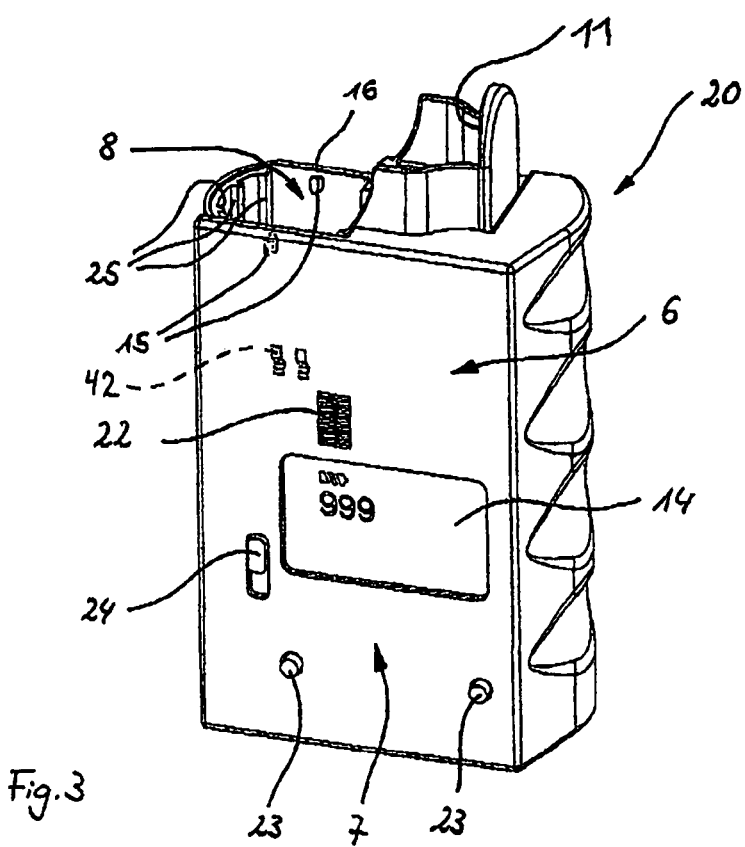
FIG. 3 shows, in isometric representation, a base housing.

To provide for sealing between the structural units, a circumferential sealing device shown in FIG. 3 is provided on the base housing 20, said sealing device being designed as a rubber profile 16 and serving to prevent undesired flow of air into the mouthpiece 5. Thus, depending on the requirements of the medium dispensing operation, the stream of air can flow in a turbulent or laminar stream into the mouthpiece 5 as a function of the configuration of the air inlet 22 and of the receiving chamber 8 and of the plug-in portion 4.

The base housing 20 is provided with a closure means for the mouthpiece opening 12 of the mouthpiece 5. The mouthpiece 5 serves as interface to the user of the dosing device 1 and has medium-conveying surfaces 21 for the medium to be dispensed. Since the medium to be dispensed can in particular involve active substances, deposition of these active substances on the medium-conveying surfaces must be taken into consideration. As a consequence of deposition of the active substance, combined with microbes from the environment of the dosing device 1, contamination of the medium-conveying surfaces 21 cannot be ruled out. To minimize the period of exposure of the medium-conveying surfaces 21 to the environment and thus reduce the risk of contamination, a closure means 11 for the mouthpiece opening 12 of the mouthpiece 5 is provided. The closure means 11 closes off the mouthpiece opening 12 shortly after the dispensing of the medium has concluded, so that only a final and in particular uncritical number of microbes can act on the medium-conveying surfaces 21.

For using the dosing device 1 according to the illustrative embodiment shown in FIGS. 1 to 3, the ultrasonic atomizer 2 with plug-in portion 4 is initially inserted into the receiving chamber 8 of the base housing 20. In doing this, the plug-in portion 4 is guided linearly by the guide tracks 25. As soon as the mouthpiece 5 strikes the guide pins 15 provided in the base housing 20, during the process of inserting the plug-in portion 4, the mouthpiece has to be swivelled into the position shown in FIG. 2 in order to permit complete insertion into the receiving chamber 8. The guide pins 15 slide into the locking groove 9 of the mouthpiece 5 and establish a form-fit connection between the two structural units. If the ultrasonic atomizer 2 is inserted correctly into the receiving chamber 8 of the base housing 20, locking between the plug-in portion 4 and the base housing 20 can be effected via the slide switch 24. The slide switch locks the plug-in portion 4 and at the same time enables the electrical/electronic function of the dosing device, so that the latter can be put into operation. In this way, a safety function is provided and operation of the dosing device 1 is possible only when the ultrasonic atomizer 2 has been correctly locked. Moving the slide switch 24 to the unlocked position puts the dosing device and thus the ultrasonic atomizer 2 out of operation and permits removal of the ultrasonic atomizer from the base housing 20.

In the absence of any force exerted by the user, the spring element 19 ensures that the mouthpiece 5 is swivelled in such a way that the mouthpiece opening 12 is closed off by the cover plate 11 against contamination from the environment. This mouthpiece position corresponds to the rest position of the dosing device. In this rest position, a sensor means (not shown) sends a position signal to the electronic control system 6 so that no dispensing of medium can take place. The sensor means can be designed as a switch which transmits a corresponding switch signal to the electronic control system 6 or some other kind of control unit.

By swivelling the mouthpiece 5 from the rest position, the mouthpiece opening 12 is freed. A range of swivel of the mouthpiece 5 is limited here by the interaction between the slide guide, formed as locking groove 9 in the mouthpiece 5, and the guide pin 15. By means of the locking groove 9, a form-fit locking between the locking groove 9 and the guide pin is ensured over almost the entire range of swivel of the mouthpiece 5.

By actuating one of the push buttons 23, the user can now activate the dosing device and, if so required, can further actuate the press buttons 23 to act on the dosing of medium, particularly by incremental increase or reduction of the quantity of medium that is to be dispensed. The user can then put his lips firmly round the mouthpiece 5 and, by breathing in, can generate a stream of air through the air inlet 22 and the downstream air channel of the dosing device and into the mouthpiece 5. The developing stream of air acts on a measurement means which sends a control signal to the electronic control system 6 in order to execute the medium-dosing operation. From the electronic control system 6, an activation signal is then transmitted via the contact tongues 42 and contact surfaces 10 to the ultrasonic atomizer 2 and from there passed on to the delivery means 40 and/or ultrasonic chamber via the printed circuit board 26. In response to the activation signal, the delivery means delivers a quantity of medium from the container 3 of liquid. By means of an ultrasonic means (now shown), the medium is finely atomized and mixed with the stream of air. Thus, during the inhalation movement on the part of the user, medium is transported from the container 3 of liquid and into the stream of air flowing through the mouthpiece 5.

Thus, depending on the nature of the atomization and on the size of the liquid droplets resulting from the atomization, the medium can be sucked a greater or lesser distance into the user's respiratory tract. When the inhalation process ends, the mouthpiece 5 can be returned to the rest position and is closed off by the cover plate 11 until the next time that medium is dispensed.

For removing the ultrasonic atomizer 2 from the base housing 20, the mouthpiece 5 is pivoted from the rest position into the position shown in FIGS. 1 and 2 and, after cancelling the form fit between the locking groove 9 and the guide pin 15, it can then be removed from the base housing 20. Upon removal of the ultrasonic atomizer 2, the electrical contact between the spring-tensioned contact tongues in the receiving chamber 8 and the contact surfaces 10 is also automatically cancelled.

The invention claimed is:

1. A dosing device for dosing a medium, said dosing device comprising:

a first structural unit including an electrically driven delivery device, a plug-in portion enclosing therein a reservoir for storing medium to be dosed, and an applicator for dispensing the medium, the delivery device being configured to receive electrical energy required to deliver medium to the applicator;

a second structural unit including a control unit for actuating said delivery device, and an electrical energy store for electrically powering said control unit and said delivery device, said second structural unit defining therein a receiving chamber which opens through an end of said second structural unit and is configured to house said plug-in portion of said first structural unit, said first and second structural units being wholly separable from one another;

a guide arrangement cooperating between said first and second structural units to permit the coupling of said first and second structural units to one another; and an electrical interface cooperating between said first and second structural units and disposed to electrically couple said delivery device of said first structural unit to said energy store and said control unit of said second structural unit without the use of tools, said electrical interface being disposed and configured to supply electrical energy directly to said delivery device and said delivery device receiving electrical energy from said energy store via said electrical interface to thereby power and operate said delivery device upon coupling of said first and second structural units to one another.

2. The dosing device according to claim 1, wherein said guide arrangement includes a linear guide disposed on said plug-in portion and a linear guide disposed in said receiving chamber, said linear guides being configured to cooperate with one another during coupling of said first structural unit to, and during uncoupling of said first structural unit from, said second structural unit.

3. The dosing device according to claim 1, wherein said electrical interface includes an electrical contact disposed on said plug-in portion and electrically connected to said delivery device, and an electrical contact disposed in said receiving chamber and electrically connected to said control unit, said electrical contacts being disposed to electrically contact one another upon insertion of said plug-in portion into said receiving chamber.

4. The dosing device according to claim 1, wherein the receiving chamber surrounds the reservoir.

* * * * *